US012100486B2

(12) United States Patent
Pastore et al.

(10) Patent No.: US 12,100,486 B2
(45) Date of Patent: Sep. 24, 2024

(54) IDENTIFICATION OF UNKNOWN GENOMES AND CLOSEST KNOWN GENOMES

(71) Applicant: International Business Machines Corporation, Armonk, NY (US)

(72) Inventors: Vito Paolo Pastore, Lecce (IT); Mark Kunitomi, San Francisco, CA (US); Simone Bianco, San Francisco, CA (US)

(73) Assignee: International Business Machines Corporation, Armonk, NY (US)

( * ) Notice: Subject to any disclaimer, the term of this patent is extended or adjusted under 35 U.S.C. 154(b) by 230 days.

(21) Appl. No.: 17/321,371

(22) Filed: May 14, 2021

(65) Prior Publication Data

US 2022/0367011 A1   Nov. 17, 2022

(51) Int. Cl.
  *G16B 50/10* (2019.01)
  *G06F 16/28* (2019.01)
  *G16B 30/10* (2019.01)

(52) U.S. Cl.
  CPC ........... *G16B 50/10* (2019.02); *G06F 16/285* (2019.01); *G16B 30/10* (2019.02)

(58) Field of Classification Search
  USPC ....................................................... 702/19
  See application file for complete search history.

(56) References Cited

U.S. PATENT DOCUMENTS

| | | | |
|---|---|---|---|
| 2005/0267692 A1 | 12/2005 | Tsirigos et al. | |
| 2019/0303534 A1 | 10/2019 | Davis et al. | |
| 2020/0104464 A1 | 4/2020 | Kaufman et al. | |

OTHER PUBLICATIONS

Liang, Qiaoxing, et al. "DeepMicrobes: taxonomic classification for metagenomics with deep learning." NAR Genomics and Bioinformatics 2.1 (2020): lqaa009. (Year: 2020).*
Liang, Qiaoxing, et al. "DeepMicrobes: taxonomic classification for metagenomics with deep learning." Supplementary Material. NAR Genomics and Bioinformatics 2.1 (2020): lqaa009. (Year: 2020).*
Fabijańska, Anna, and Szymon Grabowski. "Viral genome deep classifier." IEEE Access 7 (2019): 81297-81307. (Year: 2019).*
"What is feature vector". Deepchecks</i>. (Aug. 5, 2021). https://deepchecks.com/glossary/feature-vector/ (Year: 2021).*
Li, Jianwei, Yan Huang, and Yuan Zhou. "A mini-review of the computational methods used in identifying RNA 5-methylcytosine sites." Current Genomics 21.1 (2020): 3-10. (Year: 2020).*
"K-mer." Wikipedia, The Free Encyclopedia. Wikipedia, The Free Encyclopedia, Aug. 18, 2023. Web. Oct. 11, 2023. (Year: 2023).*
"One-hot." Wikipedia, The Free Encyclopedia. Wikipedia, The Free Encyclopedia, Dec. 12, 2022. Web. Oct. 11, 2023. (Year: 2023).*
Altschul et al., Basic Local Alignment Search Tool, Journal of Molecular Biology 215:403-4011 (1990).
Brejova et al., Finding Patterns in Biological Sequences, Project Report for CS798g, University of Waterloo, Ontario, Canada, pp. 1-49 (2000).
Busia et al., A deep learning approach to pattern recognition for short DNA sequences, Project Report for Google AI Residency Program, University of California, Berkeley, California, pp. 1-12 (2019).
Che et al., An Anomaly Detection Algorithm for Identifying Alien Gene Clusters in Microbial Genomes, Int'l Conf. Bioinformatics and Computational Biology (BICOMP'16), pp. 31-37 (2016).
Dubinkina et al., Assessment of k-mer spectrum—applicability for metagenomic dissimilarity analysis, BMC Bioinformatics 17:38, pp. 1-11 (2016).
Fiannaca et al., Deep learning models for bacteria taxonomic classification of metagenomic data, BMC Bioinformatics 19(Suppl 7):198, pp. 61-76 (2018).
Geller et al., The external domains of the HIV-1 envelope are a mutational cold spot, Nature Communications 6:8571, pp. 1-9 (2015).
Kendall & Gal, What Uncertainties Do We Need in Bayesian Deep Learning for Computer Vision?, 31st Conference on Neural Information Processing Systems (NIPS 2017), Long Beach, California, pp. 1-11 (2017).
Ng et al., dna2vec: Consistent vector representations of variable-length k-mers, pp. 1-10 (2017), available on-line at: arXiv:1701.06279v1 [q-bio.QM].
Nweke et al., Multi-sensor fusion based on multiple classifier systems for human activity identification, Human-centric Computing and Information Sciences 9:34, pp. 1-44 (2019).
Ounit et al., Clark: fast and accurate classification of metagenomic and genomic sequences using discriminative k-mers, BMC Genomics 16:236, pp. 1-13 (2015).
Rizzo et al., A Deep Learning Approach to DNA Sequence Classification, Computational Intelligence Methods for Bioinformatics and Biostatistics, 12th International Meeting (CIBB 2015), Naples, Italy, pp. 129-140 (2015).
Tagasovska and Lopez-Paz, Single-Model Uncertainties for Deep Learning, 33rd Conference on Neural Information Processing Systems (NeurIPS 2019), Vancouver, Canada, pp. 1-12 (2019).
Wang et al., New techniques for extracting features from protein sequences, IBM Systems Journal 40(2):426-441 (2001).
Wen et al., A classification model for lncRNA and mRNA based on k-mers and a convolutional neural network, BMC Bioinformatics 20:469, pp. 1-14 (2019).
Wood and Salzberg, Kraken: ultrafast metagenomic sequence classification using exact alignments, Genome Biology 15:R46, pp. 1-12 (2014).
Yu, Segmented K-mer and its application on similarity analysis of mitochondrial genome sequences, Gene 518:419-424 (2013).

(Continued)

*Primary Examiner* — G. Steven Vanni
(74) *Attorney, Agent, or Firm* — Caleb D. Wilkes

(57) ABSTRACT

Provided is a deep learning algorithm that analyzes fragments of biological sequences. The input for the deep learning algorithm is a biological sequence fragment of unknown origin and the output is the closest known biological genome that could share phenotypic properties with the biological species of unknown origin. The workflow thus has application for genomic classification, identification of mutations within known genomes, and the identification of the closest class for unknown species.

17 Claims, 2 Drawing Sheets

(56) References Cited

OTHER PUBLICATIONS

Zhang et al., Regression via Arbitrary Quantile Modeling, pp. 1-12 (2019), available on-line at: arXiv:1911.05441v1 [cs.LG].
Du, J., Jia, P., Dai, Y. et al. Gene2vec: distributed representation of genes based on co-expression. BMC Genomics 20 (Suppl 1), 82 (2019). https://doi.org/10.1186/s12864-018-5370-x.

\* cited by examiner

IDENTIFICATION OF UNKNOWN GENOMES AND CLOSEST KNOWN GENOMES

TECHNICAL FIELD

The present invention relates generally to bioinformatics and more specifically to the use of deep learning artificial intelligence for identifying unknown and closest known genomes.

BACKGROUND OF THE INVENTION

Taxonomic classification of viral pathogens is important for public safety. For example, the ability to determine the name of a virus or another pathogen in many cases sets the course of action to be taken by governments and public service organizations in terms of food safety, treatment options in clinical cases, and the determination of the likely chains of transmission in epidemiological investigations. The diversity of living organisms poses difficulties in the ability to detect, combat, and categorize pathogens. With the decrease in the cost and the increase in the accessibility of high-throughput sequencing, the number of genomes that have been sequenced has increased rapidly. With an increase in genomic sequencing data comes an increase in methods to scale the data. The sheer amount of data (there are >100,000 genomes in GenBank as of November 2017) presents an opportunity to capture the diversity of viruses, bacteria, fungi, etc., but the large volume of data also presents a challenge for the development of methods that computationally derive meaningful features from this data. Use of standard bioinformatic classification software is dependent upon large-scale databases that incorporate all incoming genomic data from organisms of interest. As the data grows, the computational load of these methods becomes increasingly inviable for purposes of storage, memory, and computation time.

SUMMARY OF THE INVENTION

In one aspect, the present invention relates to a method for classifying biological sequences comprising: providing a training set of biological sequences related to a biological sequence of interest; dividing the training set and the biological sequence of interest into sequence fragments; extracting feature vectors from the training set sequence fragments and from the biological sequence of interest sequence fragments; identifying feature vectors extracted from the biological sequence of interest sequence fragments that correspond to feature vectors extracted from the training set sequence fragments; establishing a threshold value comprising an average degree of divergence of the feature vectors from the biological sequence of interest sequence fragments from the training set sequence fragments, wherein the threshold value sets a percentage for classification of the biological sequence of interest sequence fragments; and detecting an anomaly from within the extracted features of the sequence fragments of the biological sequence of interest, wherein the anomaly are sequence fragments that fall outside of the threshold value.

In another aspect, the present invention relates to a computer program product for classifying biological sequences, the computer program product comprising one or more computer readable storage media, and program instructions collectively stored on the one or more computer readable storage media, the program instructions comprising: program instructions for training a deep learning algorithm with a training set of sequence fragments related to a biological sequence of interest, wherein the deep learning algorithm extracts feature vectors from the training set; program instructions for applying the trained deep learning algorithm to sequence fragments of the biological sequence interest and obtaining extracted feature vectors from the sequence fragments; program instructions for clustering the extracted feature vectors from the training set and the biological sequence of interest and computing an average degree of divergence of the extracted feature vectors of the biological sequence of interest from the extracted feature vectors of the training set; program instructions for establishing a threshold value based upon the average degree of divergence, wherein the threshold value sets a percentage for classification of the sequence fragments of the biological sequence of interest; and program instructions for detecting an anomaly from within the extracted features of the sequence fragments of the biological sequence of interest, wherein the anomaly are sequence fragments that fall outside of the threshold value.

In a further aspect, the present invention relates to a computer-implemented method for classifying biological sequences comprising: training a deep learning algorithm with a training set of sequence fragments related to a biological sequence of interest, wherein the deep learning algorithm extracts feature vectors from the training set; applying the trained deep learning algorithm to sequence fragments of the biological sequence interest and obtaining extracted feature vectors from the sequence fragments; clustering the extracted feature vectors from the training set and the biological sequence of interest and computing an average degree of divergence of the extracted feature vectors of the biological sequence of interest from the extracted feature vectors of the training set; establishing a threshold value based upon the average degree of divergence, wherein the threshold value sets a percentage for classification of the sequence fragments of the biological sequence of interest; and detecting an anomaly from within the extracted features of the sequence fragments of the biological sequence of interest, wherein the anomaly are sequence fragments that fall outside of the threshold value.

Additional aspects and/or embodiments of the invention will be provided, without limitation, in the detailed description of the invention that is set forth below.

DETAILED DESCRIPTION OF THE INVENTION

Figure 1:
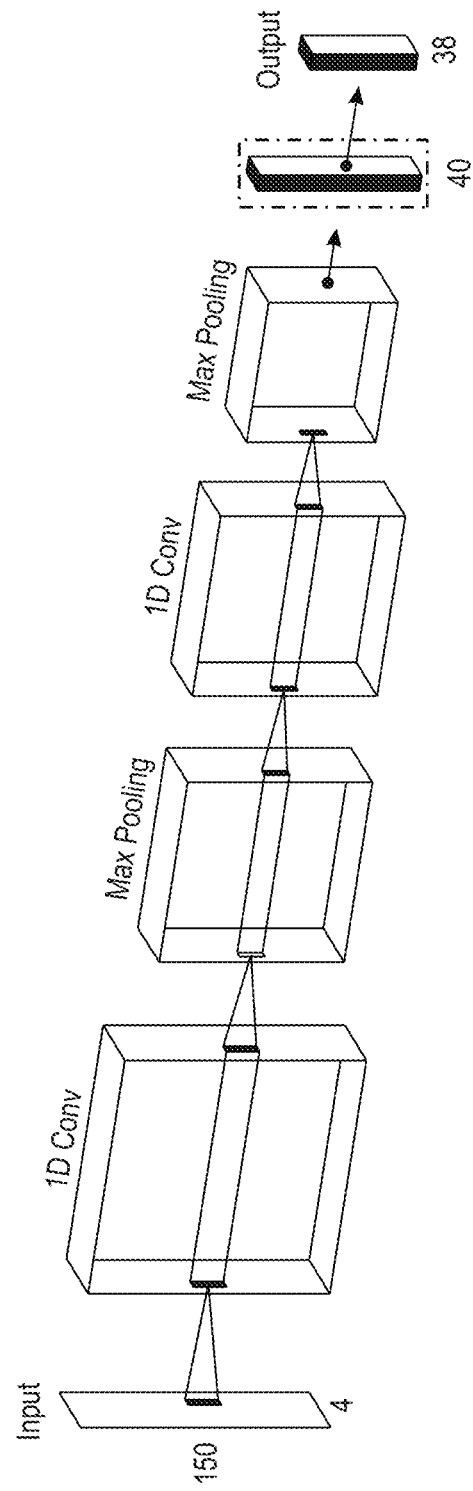
FIG. 1 is a schematic representation of a one-dimensional convolution neural network (1-D CNN) with max pooling that identifies and classifies 40 viral genomes from a 150-mer viral genome sample.

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," "comprised," "comprises," and/or "comprising," as used in the specification and appended claims, specify the presence of the expressly recited components, elements, features, and/or steps, but do not preclude the presence or addition of one or more other components, elements, features, and/or steps.

As used herein, the term "deep learning" refers to an artificial intelligence (AI) function that mimics the workings of the human brain in processing and categorizing data. Deep learning-based AI is able to learn from data that is unstructured and unlabeled. In operation, deep learning-based AI programs find correlations between inputs and outputs by learning to approximate an unknown function (f(x)=y) between any input x and any output y, assuming they are related by correlation or causation.

As used herein, the term "neural network" refers to a deep learning classification algorithm that is modeled after the human brain with a collection of simulated neurons. Each neuron is a node that is connected to other nodes via links that are analogous to biological axo-synapse dendrite connections. Each link has a weight, which determines the strength of one node's influence on another. Neural networks learn (i.e., are trained) by processing examples, each of which contains a known input and output forming probability weighted associations between the input and the output. In operation, a neural network groups unlabeled input data according to similarities among example inputs, automatically extracts features from the groups, clusters groups with similar features, and classifies output data when there is a labeled dataset for training. The patterns recognized by a neural network are numerical and contained in vectors, which must be translated. Examples of neural network vectors include without limitation, images, sound, text, time, or combinations thereof.

As used herein, the term "convolutional neural network" or "CNN" is a classification algorithm where a neural network is applied to analyzing data. A CNN can be one-dimensional (1-D), two dimensional (2-D), or three dimensional (3-D). Generally, 1-D CNNs are used on audio and text data; 2-D CNNs are used on image data; and 3-D CNNs is used on 3-D image data. CNNs use convolution kernels, which are learnable filter matrices that are used to extract features from the input data and make predictions from the extracted features. A kernel matrix moves along input data by a stride value. For example, if a stride value is 2, a kernel moves by two columns of data in the input matrix. With 1-D CNNs, the input data is one-dimensional and the convolution kernel slides in one dimension along the axis of time. With 2-D CNN, the input data is two-dimensional and the kernel slides in two dimensions along the axes of height and width. With 3-D CNN, the input data is three-dimensional and the kernel slides in three dimensions along the axes of height, width, and volume.

Generally, convolutional layers convolve input and pass its result to the next layer. While fully connected feedforward neural networks can be used to learn features and classify data, CNNs regularize multilayer fully connected networks (also known as perceptrons) where each neuron in one layer is connected to all neurons on the next layer. The nature of the fully connected layers of a CNN leads to overfitting data, which must be regularized. CNNs regularize by taking advantage of the hierarchical pattern in data to assemble complex patterns using smaller and simpler patterns. A CNN consists of an input layer, hidden middle layers, and an output layer. The hidden middle layers perform the convolutions. After passing through a convolutional layer, the data become abstracted to a feature map, which is the output of the convolution kernel that was applied to the previous layer.

It is to be understood that all references to deep learning made herein include neural networks and CNNs as subsets of deep learning-based AI.

As used herein, the term "max pooling" refers to an operation that is added to CNNs following individual convolution layers. Because max pooling is added after a convolution layer, the output from the convolution operation is the input to the max pooling operation. When added to a CNN, max pooling reduces the data output from the previous convolution layer. When max pooling output is input into a convolution layer, the CNN is analyzing larger areas of the original input image thus reducing the number of parameters for analysis and the computational load on the CNN system. Max pooling also reduces the overfitting inherent in CNN analyses by preserving the high data values going forward while discarding the lower values.

As used herein, the term "Y percentile" refers to a deep learning regression variable. In deep learning, input variables are identified with X and output values with Y such that Y=f(X), where f(X) is the prediction value and Y is a parameter to be tuned. For example, where the Y percentage for a prediction value is set at 75%, there is a 75% chance that the output value is below the prediction value and a 25% chance that the output value is above the prediction value.

As used herein, the terms "k-mer" refers to a string of nucleotides (i.e., ATGC) of length k contained within a DNA sequence. For purposes of illustration, the sequence AATCGCC has seven monomers (A, A, T, C, G, C, C), six 2-mers (AA, AT, TC, CG, GC, CC), five 3-mers (AAT, ATC, TCG, CGC, GCC), four 4-mers (AATC, ATCG, TCGC, CGCC), three 5-mers (AATCG, ATCGC, TCGCC), two 6-mers (AATCGC, ATCGCC), and one 7-mer (AATCGCC).

As used herein, the term "one-hot encoding" refers to a computational method for pre-processing categorical variables such that within a group of bits one variable is identified as a single high (1) (the "one-hot") while all the others are low (0). One-hot encoding enables non-numeric input variables, such as for example nucleotides, to become numeric values suitable for computational analyses in AI systems. Table 1 provides an example of a one-hot coding binary matrix for the 7-mer AATCGCC. As shown therein, the nucleotides undergoing analysis are represented by the value (1) while the remaining nucleotide have the value (0).

TABLE 1

| | \multicolumn{7}{c}{AATCGCC} | | | | | | |
|---|---|---|---|---|---|---|---|
| A | 1 | 1 | 0 | 0 | 0 | 0 | 0 |
| T | 0 | 0 | 1 | 0 | 0 | 0 | 0 |
| G | 0 | 0 | 0 | 0 | 1 | 0 | 0 |
| C | 0 | 0 | 0 | 1 | 0 | 1 | 1 |

As used herein, the term "genomic sequence" refers to the order of nucleotide bases present in the entire genome of any living organism. Examples of genomes contemplated under the methods described herein include, without limitation, animals, insects, plants, and microbes. Examples of microbes include, without limitation, viruses, bacteria, archaea, fungi, molds, protozoa, helminths, and prions. The term "gene sequence" refers to the order of nucleotide bases that completely or partially control the expression of one or more traits in any living organism. The term "protein sequence" refers to the amino acid sequence of all of part of a protein or peptide. The term "protein domain sequence"

refers to a conserved part of a protein sequence that is stable and folds independently of the rest of the protein sequence.

In the discussions that follow, viral sequences will be used as exemplary sequences, but it is to be understood that the present invention has application to non-viral gene sequences as described herein.

Deep learning has the capability to reduce the computational load required for taxonomic classification. By learning the predictive features of data, deep learning approaches are able to capture complex latent features that simplistic bioinformatic approaches can only approximate though breadth of the data. One deficiency of deep learning classifiers is the general inability to call a given observation as an outlier relative to the data that the model has been trained on. A naïve deep learning classifier will make a prediction based on the best available candidate. This approach is problematic in the case of species, such as viral species that have not yet been discovered. The ability to determine characterizing features of viral genomes and populations in the context of diversity, together with the ability to detect outlier sequences, is beneficial for public health and food safety.

State-of-the-art methods of sequence-based classification of taxonomic identification are performed by comparing a query sequence to a reference database of ground truth labeled sequences by either alignment or pseudo-alignment. Alignment methods are generally considered the most accurate and interpretable while pseudo-alignment methods offer greater speeds at the cost of some interpretability and variability due to parameter choices. Both of alignment and pseudo-alignment methods work well when comparing sequences of high similarity. When the query is of a different species than any of the species within the reference database, there is no mechanism for recognition of this situation. Classification by Machine Learning Classification (MLC) performed by deep learning models offers an alternative to both alignment and pseudo-alignment methods in that they are both fast and lightweight in terms of storage and memory usage. Several deep learning-based classification models have been developed for bacteria; however, all of these models are trained to classify only a single region of the genome encoding the 16S gene. The use of a single gene that maintains a relatively tight distribution of sizes is useful for training deep learning models because deep learning models are dependent upon data structured in an invariant format, such as matrices or tensors of fixed dimensionality; however, classification by a single gene is ineffective and inappropriate for general taxonomic classification.

For general taxonomic classification, the gene selected must be: (i) universally present in the genomes of interest; (ii) of similar length between all examples; and (iii) representative of the diversity of the taxonomic classification labels for training purposes (e.g., each taxon must have a uniquely defining sequence for the gene otherwise it cannot be differentiated from a different taxon). Observed differences in gene sequences are the cumulation of mutation rate (which is different between organisms), natural selection (which is dependent upon environment), and time; all of which are not constant between different genes. Genes with low rates of mutation will provide poor resolution for closely related organisms and genes with high rates of mutation will provide poor resolution for distantly related organisms.

The deep learning workflow described herein implements a method of analyzing fragments of a biological sequence for genome classification and outlier anomaly detection. With outlier anomaly detection, the input is a biological sequence fragment of unknown origin and the output is the closest known biological genome that could share phenotypic properties with the biological species of unknown origin. The workflow has application for genomic classification, identification of mutations within known genomes, and the identification of the closest class for unknown species. The use of a deep learning algorithm in the workflow allows the workflow to be scalable for large data sets.

Figure 2:
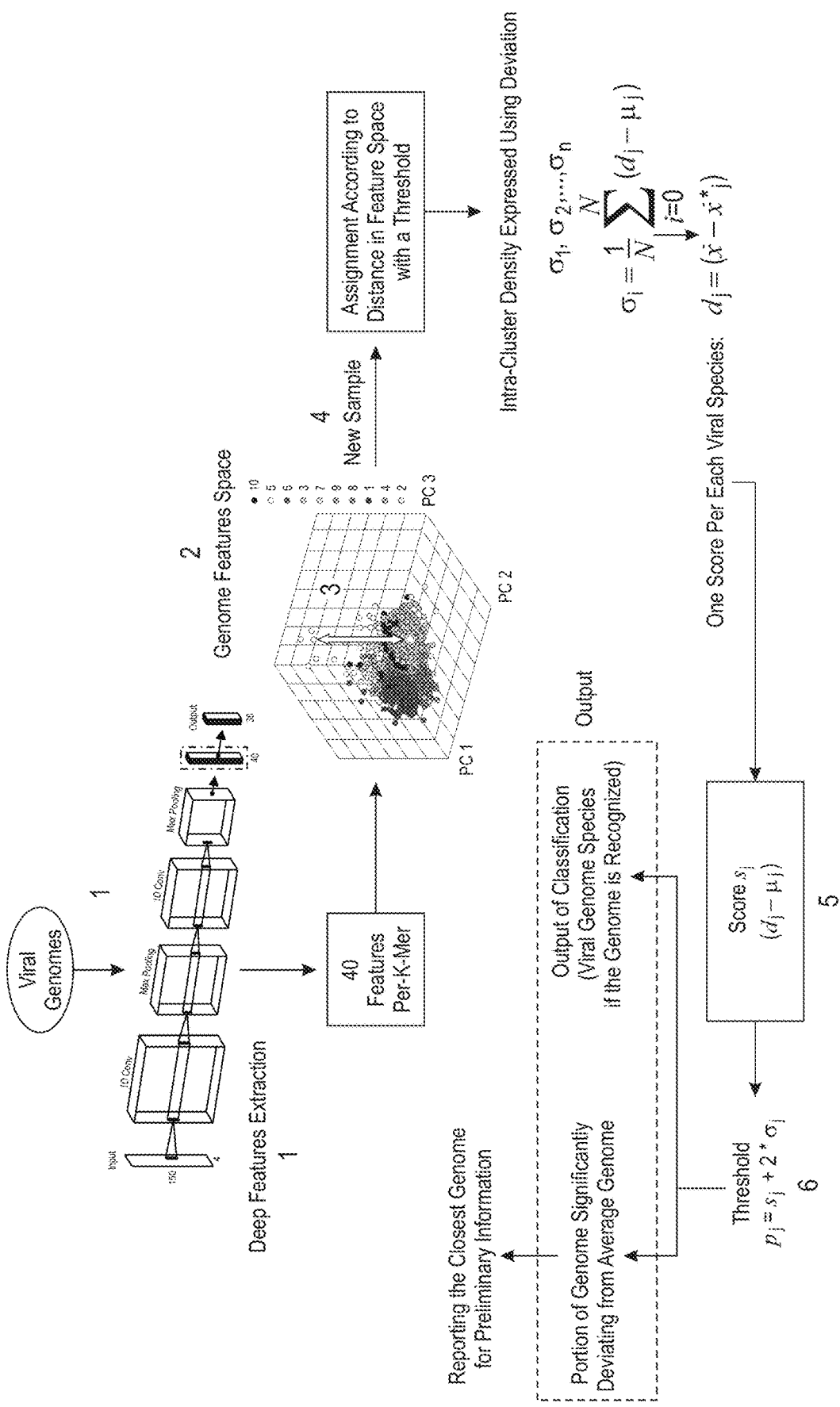
FIG. 2 is a schematic representation of a workflow that identifies and classifies the closest viral genomes to the 40 viral genomes identified and classified by the 1-D CNN.

The first step in implementing the workflow is the training of a deep learning algorithm to carry out deep feature extraction. FIGS. 1 and 2, the deep learning algorithm is a 1-D CNN deep features extractor 1 with two convolution layers and two max pooling layers inserted after each convolution layer to reduce CNN overfitting. In order for the 1-D CNN to be able to extract features in the form of feature vectors from a biological sequence fragment, the 1-D CNN must be trained on sequence data. For pre-processing, the sequence fragments to be analyzed are divided into k-mers comprised of four bases, which are organized into a binary matrix with one-hot encoding. In FIGS. 1 and 2, a 150-mer viral sequence fragment is used for training the 1-D CNN to identify and classify viral genomes. After organizing the 150-mer fragment into the pre-processing binary matrix with one-hot encoding, the 150-mer sequence is input into the 1-D CNN. After processing through the two convolution and max pooling layers, the 1-D CNN output is a 40-mer viral sequence fragment.

The extracted features from the training set are mapped into a genome features space 2, fragment by fragment, with the computing of the corresponding centroids 3. The genome features map in FIG. 2 shows ten class clusters each of which has its own calculated centroid. For each of the extracted features mapped in the genome features space, the average degree of intra-cluster density is computed according to Formula (1):

$$\sigma_i = \frac{1}{N} \sum_{i=0}^{N} (d_j - \mu_j) \tag{1}$$

where d is the Euclidian distance computed among the feature j; $\mu_j$ is the average value of the distance for the N samples; N is the number of training samples; and $\sigma_i$ is the output $\sigma_0, \sigma_1, \ldots \sigma_M$, where M is the total number of features. The average degree of intra-cluster density corresponds to the standard deviation computed among the distribution of the distances with respect to the centroid.

Following training of the convolution algorithm and mapping of the extracted features, a new and unknown sample 4 may be introduced into the workflow for classification. Like the training sample, the new sample is pre-processed into a binary matrix, run through the deep features extractor, and mapped as into the genome features map as clusters. The intra-cluster density of the new sample is also calculated according to Formula (1). Unlike the training data, which is unlabeled, the new unknown sample is labeled.

To classify the new sample, an output score 5 is computed as the difference between each of the input features in the new sample and the average value of the training distribution among each feature. For an input with a total number of features M, the closest class X to the input has an output score for each feature $s_j$ computed according to Formula (2):

$$s_j = (d_j - \mu_j), \text{ with output } s_0, s_1, \ldots s_M, \tag{2}$$

where d is the Euclidian distance computed among the feature j and $\mu_j$ is the average value of distance for the training samples.

To identify anomalies, a threshold value θ is heuristically determined from the average degree of divergence of the new sample from the training samples where the average degree of divergence is the difference between the score and the degree of intra-cluster density. The threshold value θ is a percentile value for the training samples that is above the Y percentile (e.g., 75%) where Y is a parameter to be tuned. For a sample input with features M, the degree of divergence $deg_j$ is computed according to Formula (3):

$$deg_j = s_j - \sigma_j, \text{ with output } deg_0, deg_1, \ldots deg_M, \quad (3)$$

where $s_j$ is the output score for each feature j and $\sigma_j$ is the degree of intra-cluster density for each feature j. The score for an anomaly is calculated according to Formula (4):

$$s_j > \theta * deg_j^*, \text{ with output } deg_0^*, deg_1^*, \ldots deg_M^* \quad (4)$$

where if the degree of divergence $deg_j^*$ is higher than the score $s_j$, then the feature is considered as an anomalous fragment. The values θ and M* are determined heuristically with a linear search under the constraint that a specific number of k-mers among the training genomes are outliers. For example, with reference to the 40-mer output of FIGS. 1 and 2, setting the threshold for the convolution algorithm at 95% would have the algorithm run until the number of classified samples to anomalies is 95:5. The result of the 95% threshold is classification of 38 different viral genomes (the 95%) from the 40-mer output with two viral genomes (the 5% of the 40-mer output) representing unknown viral genomes (Example 1). If an unknown viral genome sample is anomalous for more than M* features, the genome is labeled as anomalous and the closest genome will be the one determined as the closest class X (Example 2). The output 7 of the workflow is: (i) the viral genome species if the genome is recognized as belonging to the training (known) set, or (ii) the closest known genome in the case of an anomaly.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, a graphics processing unit (GPU), programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables, experimental error and deviations should be considered. All components were obtained commercially unless otherwise indicated.

Example 1

Classification of an Unknown Viral Isolate

An unknown viral isolate (e.g., either a novel virus or an example of a previously identified viral species) was classified according to the biological classification process described herein. For pre-processing, i.e., building the known viruses features space, 100 viral genomes belonging to 40 viral species were collected. The 100 viral genomes were represented using k-mers. The genome k-mers were divided into a sequence of 150 bases with a 25-base overlap. Each sequence was converted into a binary image of size 4 (representing the number of bases ACGT)×150 (the number of k-mers, i.e., the length of the sequence).

The sequences were processed through a 1D CNN (referred to herein as "the neural network") as described herein, which mapped the genomes through the neural network and produced a set of 40 features for each of the sequences where the sequences of the 40 features correspond to a 40-dimensional vector where (i) each viral genome belonging to each viral species was mapped into 40 features; and (ii) centroids were calculated for each of the known genomes in the mapped space.

For each of the known viral species, the standard deviation of the distance from a centroid to its correspondent class was computed. This was done by computing the Euclidean distance between the centroid for a species the k-mers (i.e., from the mapped 40 features) extracted from the genomes belonging to that species.

Next, for the unknown viral species, the genome for the unknown viral species was split into k-mers and converted to binary images. For each of the k-mers, the neural network was used to classify each k-mer as belonging to one of the known species or to an unknown species, with the output being the most likely species for the unknown viral species. The unknown sequence was then mapped to the 40-features space described above. For each of the 40 features, a score was computed; the score representing the difference between the unknown genome feature and the average value of training sequences belonging to a predicted class. A degree of divergence was also calculated for each of the 40 features; the degree of divergence being the difference between the score and the degree of density, as calculated with Formula (3). The computed degree of divergence for each of the 40 features was then compared to the threshold for the predicted class. The threshold was computed heuristically based on the average degree of divergence for the training samples. For the training samples, the distance from the mean was set at 95% (i.e., a value above the 75% Y percentile) and the convolution algorithm ran until the number of classified samples to anomalies was 95:5 resulting in classification of 38 viral genomes out of the 40 features space with two viral genomes representing unknown genomes (and possible anomalies) (FIGS. 1 and 2).

Example 2

Determining if an Unknown Viral Genome is a Viral Anomaly

For the two unknown viral genomes from Example 1, if one (or both) have a degree of divergence that is higher than the score (calculated as previously described herein), then the unknown viral genome is considered to be an anomalous fragment. If the unknown viral genome is similar to the predicted species, but is significantly different from the known viral genomes included in the training set, the unknown viral genome could be a mutation of a known virus or a virus sharing some feature with the predicted species.

As described in Example 1, once the training is performed, the set of thresholds for the known genomes is determined. For each viral genome sample, the trained neural network is used for classification by assigning each genome to the most likely class. Next, the score and the degree of divergence is computed as previously described herein. Finally, the degree of divergence is compared to the correspondent threshold to assess if the unknown viral genome is an anomaly.

We claim:

1. A computer-implemented method comprising:
training a deep learning model via inputting a training set of biological sequence fragments into the deep learning model,
   wherein the deep learning model converts the biological sequence fragments into k-mers one-hot encoded into a binary matrix,
   wherein the deep learning model extracts feature vectors from the biological sequence fragments of the training set,
   wherein the deep learning model is implemented on a computer,
   wherein the deep learning model maps the extracted feature vectors into a genome features space to identify clusters of extracted features,
   wherein the deep learning model computes an intra-cluster density for each extracted feature from the training set mapped in the genome features space,
   wherein the training is supervised training that uses labels of the training set to respectively associate the extracted features with genomes of the training set,
   wherein the training comprises the deep learning model determining an average training value of a training distribution among each of the extracted features, and
   wherein the training comprises the deep learning model heuristically determining a respective first threshold value for each of the extracted features from the training set; and
inputting a sample set of biological sequence fragments into the trained deep learning model, wherein the sample set of the biological sequence fragments comprises a first sample and a second sample, wherein, in response to the inputting of the sample set, the trained deep learning model:
   converts the first sample and the second sample into k-mers one-hot encoded into a respective binary matrix,
   classifies each k-mer of the first sample and the second sample as a known k-mer from the training set or an unknown k-mer,
   predicts a first class for the first sample and a second class for the second sample based on the labels of the training set,
   maps the first sample and the second sample into the genome features space to determine, respectively, first values for the first samples for the features and second values for the second samples for the features,
   computes an output score for the first sample for each of the features and for the second sample for each of the features, wherein the output score is the difference between the respective first or second value and the average training value for the respective feature for the predicted first or second class, respectively,
   computes a respective degree of divergence for the first sample for each of the features and for the second sample for each of the features, the respective degree of divergence being a difference between the respective output score of the first or second sample for the feature and the intra-cluster density for the feature,
   compares the degrees of divergence of the first and the second samples for each of the features to the respective first threshold values that were heuristically determined from the training set,
   in response to the comparing of the degrees of divergence for the first sample to the first threshold values not indicating an anomaly, provides for the first sample a classification output comprising the predicted first class, and
   in response to the comparing of the degrees of divergence for the second sample to the first threshold values indicating an anomaly, provides for the second sample a classification output comprising an indication of an anomaly and the predicted second class as a closest genome to the second sample.

2. The method of claim 1, wherein the biological sequence fragments are selected from the group consisting of a genomic sequence, a gene sequence, a protein sequence, and a protein domain sequence.

3. The method of claim 2, wherein the genomic sequence is a microbe genomic sequence.

4. The method of claim 1, wherein the deep learning algorithm is a convolution neural network.

5. The method of claim 4, wherein the convolution neural network comprises a max pooling algorithm.

6. The method of claim 1, wherein the comparing of the degrees of divergence to the respective first threshold values comprises:
   counting a number of instances in which the degree of divergence for a feature exceeds the first threshold value for the feature, and
   comparing the number of instances to a second threshold value, wherein the comparing of the degrees of divergence to the first threshold value does not indicate an anomaly when the number of instances does not exceed the second threshold value, and wherein the comparing of the degrees of divergence to the first threshold value does not indicate an anomaly when the number of instances does not exceed the second threshold value, and wherein the comparing of the degrees of divergence to the first threshold value indicates the anomaly when the number of instances exceeds the second threshold value.

7. The method of claim 6, wherein the second threshold value is determined heuristically with a linear search.

8. The method of claim 7, wherein the heuristic determinations of the first and the second threshold values are determined under the constraint that a specific number of k-mers among the genomes of the training set are outliers.

9. A computer program product comprising one or more computer readable storage media and program instructions collectively stored on the one or more computer readable storage media, the program instructions comprising:
   program instructions for training a deep learning model via inputting a training set of biological sequence fragments into the deep learning model,
      wherein the deep learning model converts the biological sequence fragments into k-mers one-hot encoded into a binary matrix,
      wherein the deep learning model extracts feature vectors from the biological sequence fragments of the training set,
      wherein the deep learning model is implemented on a computer;
      wherein the deep learning model maps the extracted feature vectors into a genome features space to identify clusters of extracted features, wherein the deep learning model computes an intra-cluster density for each extracted feature from the training set mapped in the genome features space, wherein the training is supervised training that uses labels of the training set to respectively associate the extracted features with genomes of the training set, wherein the training comprises the deep learning model determining an average training value of a training distribution among each of the extracted features, and wherein the training comprises the deep learning model heuristically determining a respective first threshold value for each of the extracted features from the training set; and program instructions for inputting a sample set of biological sequence fragments into the deep learning model, wherein the sample set of the biological sequence fragments comprises a first sample and a second sample, wherein, in response to the inputting of the sample set, the trained deep learning model:

converts the first sample and the second sample into k-mers one-hot encoded into a respective binary matrix, classifies each k-mer of the first sample and of the second sample as a known k-mer from the training set or an unknown k-mer, predicts a first class for the first sample and a second class for the second sample based on the labels of the training set, maps the first sample and the second sample into the genome features space to determine, respectively, first values for the first samples for the features and second values for the second samples for the features, computes an output score for the first sample for each of the features and for the second sample for each of the features, wherein the output score is the difference between the respective first or second value and the average training value for the respective feature for the predicted first or second class, respectively, computes a respective degree of divergence for the first sample for each of the features and for the second sample for each of the features, the respective degree of divergence being a difference between the respective output score of the first or second sample for the feature and the intra-cluster density for the feature, compares the degrees of divergence of the first and the second samples for each of the features to the respective first threshold values that were heuristically determined from the training set, in response to the comparing of the degrees of divergence for the first sample to the first threshold values not indicating an anomaly, provides for the first sample a classification output comprising the predicted first class, and in response to the comparing of the degrees of divergence for the second sample to the first threshold values indicating an anomaly, provides for the second sample a classification output comprising an indication of an anomaly and the predicted second class as a closest genome to the second sample.

10. The computer program product of claim 9, wherein the biological sequence fragments are selected from the group consisting of a genomic sequence, a gene sequence, a protein sequence, a protein domain sequence, and combinations thereof.

11. The computer program product of claim 10, wherein the genomic sequence is a microbe genomic sequence.

12. The computer program product of claim 9, wherein the deep learning algorithm comprises a convolution neural network.

13. The computer program product of claim 12, wherein the convolution neural network comprises a max pooling algorithm.

14. A computer-implemented method for classifying viral sequences comprising:

training a convolution algorithm with a training set of sequence fragments related to a sequence of an unknown viral species, wherein the sequence fragments are k-mers one-hot encoded into a binary matrix and the convolution algorithm extracts feature vectors from the sequence fragments of the training set, wherein the convolution algorithm is implemented on a computer;

programming the computer to map the extracted feature vectors from the training set into a genome features space to identify clusters of extracted features and computing intra-cluster density for each extracted feature from the training set mapped in the genome features space;

inputting a sample set of sequence fragments from the unknown viral species into the computer, wherein the sample set sequence fragments are k-mers one-hot encoded into a binary matrix and the trained convolution algorithm (i) classifies each k-mer of the sample set as a known k-mer from the training set or an unknown k-mer, (ii) predicts a class for the sample set based on the training set, (iii) assigns an average training value for the predicted class, and (iv) extracts feature vectors from the sample set;

programming the computer to map the extracted feature vectors from the sample set into the genome features space to identify clusters of extracted features and computing an output score for each extracted feature from the sample set, wherein the output score is the difference between a value for an extracted feature vector from the sample set and the average training value for the predicted class;

establishing a threshold value comprising an average degree of divergence of the sample set by calculating the difference between the output score for each extracted feature of the sample set and the intra-cluster density for each extracted feature of the predicted class from the training set, wherein the threshold value sets a percentage for classification of the sequence fragments of the unknown viral species; and detecting an anomaly from within the extracted features of the sequence fragments of the unknown viral species, wherein sequences that fall outside of the threshold value represent the anomaly, wherein for the unknown viral species the classifying comprises providing an indication of the anomaly and providing a closest known viral species sequence from the training set.

15. The computer-implemented method of claim 14, wherein sequence fragments of the unknown viral species that fall within the threshold value are assigned to a known viral species sequence.

16. The computer-implemented method of claim 14, wherein the convolution algorithm is a convolution neural network.

17. The computer-implemented method of claim 14, wherein the convolution algorithm comprises a max pooling algorithm.

* * * * *